United States Patent

Wong et al.

Patent Number: 5,301,687
Date of Patent: Apr. 12, 1994

[54] MICROWAVE APPLICATOR FOR TRANSURETHRAL HYPERTHERMIA

[75] Inventors: Terence Z. Wong, Lebanon; B. Stuart Trembly, Hanover, both of N.H.

[73] Assignee: Trustees of Dartmouth College, Hanover, N.H.

[21] Appl. No.: 711,290

[22] Filed: Jun. 6, 1991

[51] Int. Cl.⁵ .................................................. A61N 1/40
[52] U.S. Cl. ........................................ 607/116; 606/33; 606/41; 607/156
[58] Field of Search ............... 128/399, 401, 783, 786, 128/794, 804; 606/27, 33, 41; 600/2, 3, 6

[56] References Cited

U.S. PATENT DOCUMENTS

| | | |
|---|---|---|
| 1,652,954 | 12/1927 | Pierce . |
| 4,140,130 | 2/1979 | Storm, III .......................... 128/404 |
| 4,204,549 | 5/1980 | Paglione ............................ 128/784 |
| 4,292,960 | 10/1981 | Paglione ............................. 600/2 |
| 4,311,154 | 1/1982 | Sterzer et al. ..................... 128/804 |
| 4,556,070 | 12/1985 | Vaguine et al. .................... 128/804 |
| 4,583,589 | 4/1986 | Kasevich ............................ 166/60 |
| 4,601,296 | 7/1986 | Yerushaimi ........................ 128/804 |
| 4,612,940 | 9/1986 | Kasevich et al. .................. 128/804 |
| 4,632,128 | 12/1986 | Paglione et al. ................... 128/804 |
| 4,662,383 | 5/1987 | Sogawa et al. .................... 128/784 |
| 4,700,716 | 10/1987 | Kasevich et al. .................. 128/804 |
| 4,776,086 | 10/1988 | Kasevich et al. .................... 29/828 |
| 4,813,429 | 3/1989 | Eshel et al. ....................... 128/736 |
| 4,823,812 | 4/1989 | Eshel et al. ....................... 128/804 |
| 4,825,880 | 5/1989 | Stauffer et al. ................... 128/804 |
| 4,967,765 | 11/1990 | Turner et al. .................. 128/786 X |
| 5,057,106 | 10/1991 | Kasevich et al. ............... 128/804 X |
| 5,150,717 | 9/1992 | Rosen et al. ...................... 128/804 |

FOREIGN PATENT DOCUMENTS 8103616 12/1981 PCT Int'l Appl. .

OTHER PUBLICATIONS

"The Effect of Air Cooling on the Radial Temperature Distribution of a Single Microwave Hyperthermia Antenna in Vivo;" Trembly et al.; International Journal Hyperthermia in press, 1990; Ms. #90-1 Revised 15 Jun. 1990, pp. 1-15.

(List continued on next page.)

*Primary Examiner*—Stephen C. Pellegrino
*Assistant Examiner*—Jeffrey A. Schmidt
*Attorney, Agent, or Firm*—Lahive & Cockfield

[57] ABSTRACT

A radiant heating apparatus for deployment within an animal body to radiate heat-producing electromagnetic energy into the body includes an antenna mounted on a catheter element and connected to an electrical transmission line having first and second conductors for feeding electrical current from a source to the antenna. The apparatus has the improvement in which the antenna comprises a first radiating element carried on the catheter element and extending from an antenna feed junction in a first direction along a first elongation axis. The first radiating element is connected to the first transmission line conductor at the feed junction and presents a first selected impedance to the feed junction. A second radiating element is carried on the catheter element and extends from the feed junction in a second direction opposite to the first direction along the first axis. The second radiating element is connected to the second transmission line conductor and presents a second selected impedance to the feed junction. The first and second radiating elements radiate electromagnetic energy outwardly from the feed junction upon being excited from the transmission line with alternating electrical current within a selected frequency range. The first and second radiating elements are arranged for presenting the first and second impedances and for providing the radiation substantially independently of the length of the catheter element inserted within the animal body beyond the full insertion of the first or second radiating elements within the animal body.

8 Claims, 2 Drawing Sheets

OTHER PUBLICATIONS

"Control of the SAR Pattern Within an Interstitial Microwave Array Through Variation of Antenna Driving Phase;" Trembly et al.; IEEE Transactions on Microwave Theory and Techniques, vol. MIT-34; No. 5, May 1986, pp. 568-571.

"Comparison of Power Deposition by In-Phase 433 MHz and Phase-Modulated 915 MHz Interstitial Antenna Array Hyperthermia Systems;" Trembly et al.; IEEE Transactions on Microwave Theory & Techniques, vol. 36, No. 5, May 1988 pp. 908-916.

"Air Cooling for An Interstitial Microwave Hyperthermia Antenna: Theory and Experiment;" Eppert et al., IEEE Transactions on Biomedical Engineering, vol. 38, No. 5, May 1991 pp. 450-460.

"The Effect of Phase Modulation on the Temperature Distribution of a Microwave Hyperthermia Antenna Array In Vivo;" Trembly et al.; International Journal Hyperthermia, In press, Mar. 30, 1990.

"Prostatron Clinical Program, The Physics of Transurethral Microwave Thermotherapy (TUMT);" Carter et al.; Nov. 1990.

MICROWAVE APPLICATOR FOR TRANSURETHRAL HYPERTHERMIA

This invention was made in part with government support under contract number NIH/NC1 R01 CA23549 awarded by the National Institute of Health. The government has certain limited rights in the invention.

BACKGROUND OF THE INVENTION

The invention relates generally to the field of non-surgical treatment techniques and, in particular, to such techniques used for hyperthermia treatment of the prostate.

More particularly, the invention provides an improved energy-radiating instrument for intracavity use to heat body tissue selectively.

Prostatic disease, malignant or benign, is relatively common in men over 50 years of age. More than 90% of all men develop benign prostatic hyperplasia (BPH) by the eighth decade of life. It is the most common cause of urinary obstruction in men, and 10–20% of men will require prostatic surgery at some time in their lives to relieve obstructive symptoms. Presently, the treatment of choice for symptomatic BPH is surgery. That many patients suffering from BPH are elderly and may not be candidates for surgery, however, suggests that non-surgical alternatives for therapy warrant consideration.

Non-surgical treatments for BPH include medications such as alpha-adrenergic antagonists, 5-αreductase blockers, and hormones as well as mechanical dilatation. Recently, hyperthermia has been suggested as a possible treatment for BPH. Although the precise mechanism by which hyperthermia causes cell death is not fully understood, heat is known to disrupt both the cellular membrane and nuclear function. Although the biological rationale for non-surgically treating malignant tumors with hyperthermia is well established, clinical evidence has recently begun to suggest that hyperthermia may also be useful in the management of symptomatic (BPH). The anatomical location of the prostate permits various approaches to be used for treating localized prostatic disease with hyperthermia. Intracavity approaches to the prostate are possible through either the rectum or the urethra.

The transrectal approach is preferable for treating prostatic cancers because the rectum can accommodate a larger instrument which in turn can heat a larger volume of tissue. Other advantages to approaching the prostate through the rectum are that most prostatic cancers lie in the posterior portion of the prostate and are therefore most accessible transrectally. The urethra offers an easily accessible central location in the prostate for monitoring temperature. Most transrectal instrument designs feature water cooling to prevent damage to the rectal mucosa.

On the other hand, while transrectal hyperthermia instruments are advantageous for treating large prostatic lesions such as cancer, the transurethral approach has significant advantages for treating BPH. First, water-cooled transrectal instruments deliver a maximum temperature several millimeters beneath the rectal mucosa and in the posterior prostate, whereas transurethral microwave instruments deliver maximum temperature periurethrally and concentrate the hyperthermia around the symptomatic lesion. Secondly, transurethral instruments can be easily localized within the prostate using a balloon catheter and/or imaging techniques. This is more efficient than transrectal instruments which must be properly "aimed" at the prostatic lesion. Finally, the transurethral approach is less likely to cause complications resulting from damages to the rectal mucosa.

One problem facing known techniques for treating the prostate with hyperthermia is that the performance of known microwave radiating instruments, e.g. employing antennas, is a function of insertion depth. For optimum radiation, the antenna is to have antenna sections that are equal in length and that correspond to a quarter wavelength in the composite tissue/catheter medium. In typical practice, however, the length of one antenna section is dependent upon the depth to which the antenna is inserted into the patient. This insertion depth is determined by the clinical situation.

When insertion depth is not ideal based on theoretical calculations governing the operation of known transurethral microwave instruments, several problems are encountered. Antenna performance can be reduced due to increased reflected power at the antenna junction, which results in increased power requirements and ohmic heating of the antenna feedline. Clinically, this often results in pain for the patient, particularly at the entrance site of the catheter which the instrument employs to display the antenna sections. In severe situations, ohmic heating of the antenna feed-line can damage the patient's external sphincter making it difficult or impossible for the patient to voluntarily obstruct urine flow. Another problem is that as insertion depth is changed, the impedances presented by the antenna sections become unbalanced. This causes one antenna section to radiate preferentially, and displaces the heating pattern away from the desired pattern that occurs with balanced radiation.

It is, therefore, an object of the invention to provide a microwave hyperthermia instrument for intracavity use that radiates energy independently of insertion depth.

It is another object of the invention to provide such an instrument that limits the area over which energy is radiated.

It is still another object of the invention to provide such an apparatus that can be precisely positioned within a patient.

A further object is to provide a transurethral instrument having the foregoing features.

Other objects of the invention will, in part, be obvious and will, in part, appear hereinafter.

SUMMARY OF THE INVENTION

These and other objects are achieved by the present invention which features a medical treatment device for insertion into an animal body. The device radiates electromagnetic energy to heat body organs and other tissue.

The device has an antenna arranged on a catheter-like feed stem. The antenna radiates the heat producing electromagnetic energy when powered by an electronic source that usually is located outside the body being treated.

The structure of the antenna is such that the pattern of radiation, the polarization of radiation, and the antenna impedance are substantially uniform, as is desired, as the length of the feed stem within the body is changed as occurs to obtain lesser or deeper insertion of the antenna.

The invention attains these and other advantages with a dipole-type antenna in which one conductor, of a two-conductor transmission line fed from the source, feeds a radiating choke element of the antenna. The other feed-line conductor feeds across a gap in the antenna to a second radiating element. The two radiating elements present selected impedances to the feed line. In most instances, it is preferred that the two radiating elements present substantially equal impedances to the feed line.

A preferred embodiment has a coaxial feed line. The outer conductor of the coaxial feed line connects, at one side of the antenna gap, to a tubular radiating element that extends like a triaxial outer conductor, from the gap back in the direction of the source and is disposed outside the outer conductor of the coaxial transmission line. The inner conductor of the coaxial transmission line feeds, in the antenna, across the unshielded gap to the second tubular radiating element. This radiating element extends away from the gap in a direction opposite to the first radiating element. Thus, the two radiating elements are aligned on opposite sides of the gap. The second, distal, element is a conductive stub and the first, proximal, element is a conductive sleeve disposed over the feed line with an open circuit between the coaxial outer conductor and the end of that proximal element that is remote from the gap. The antenna has a feed junction located at the distal end of the first tubular radiating element, where the inner conductor is exposed.

Typically, dielectric supporting materials such as electrically nonconductive plastics, fill the space between the inner and outer conductors of the coaxial feed line and the space between the coaxial outer conductor and the first radiating element that extends outwardly over the outer conductor for a short length. Further, a nonconductive protective sheath typically of pliable plastic polymer, encloses the antenna elements. Further, it is preferred that the two tubular radiating elements have essentially the same outer diameter and essentially the same physical length. That length is dimensioned to be a substantially resonant structure, i.e., with reference to a quarter wavelength, at a frequency within the desired operating range.

BRIEF DESCRIPTION OF THE DRAWING

These and other features of the invention will be more fully appreciated by reference to the following detailed description which is to be read in conjunction with the attached drawing and in which.

DESCRIPTION OF ILLUSTRATED EMBODIMENT

Figure 1:
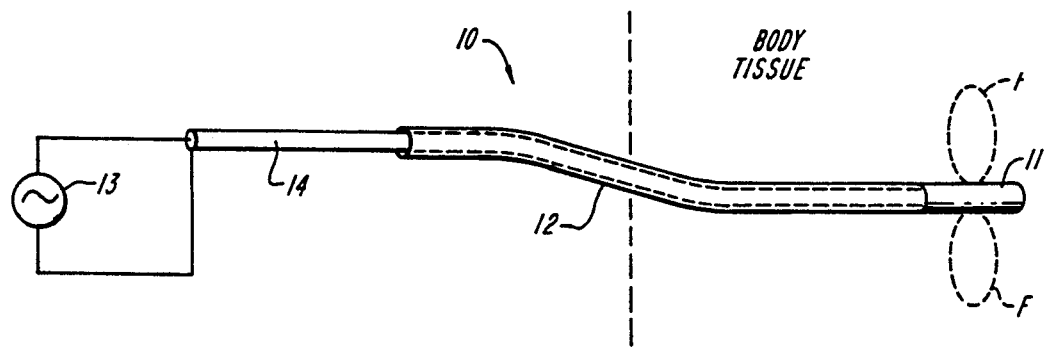
FIG. 1 is a schematic depiction of a transurethral microwave instrument constructed in accordance with the teachings of the present invention deployed within body tissue.

In one aspect, shown in FIG. 1, the invention features a radiant heating instrument 10 for deployment within an animal body, such as a human, and typically by way of a body cavity or passage, for radiating heat-producing electromagnetic energy into the body. The instrument includes an antenna 11 mounted on a catheter element 12 and connected to an electrical transmission line 14 for feeding electrical current from microwave a source 13 to the antenna 11. The instrument radiates energy from the antenna 11 with a selected field pattern F within the animal body.

Figure 2:
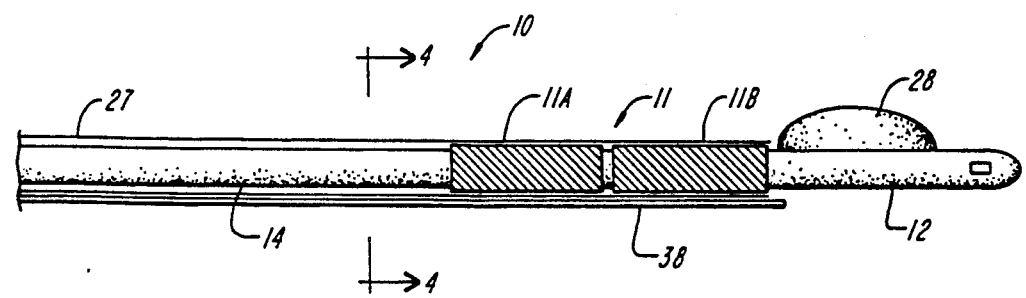
FIG. 2 is an enlarged schematic view of the transurethral microwave instrument shown in FIG. 1.

FIG. 2 shows the radiant heating instrument 10 constructed in accordance with the invention. The illustrated instrument 10 has an antenna elements 11A and 11B mounted on Foley-type catheter 12 and connected to a coaxial transmission feed line 14. While a Foley catheter is shown, other supporting envelopes suitable for deploying the feed-line 14 and antenna elements 11A and 11B within an animal body can be used.

Figure 3:
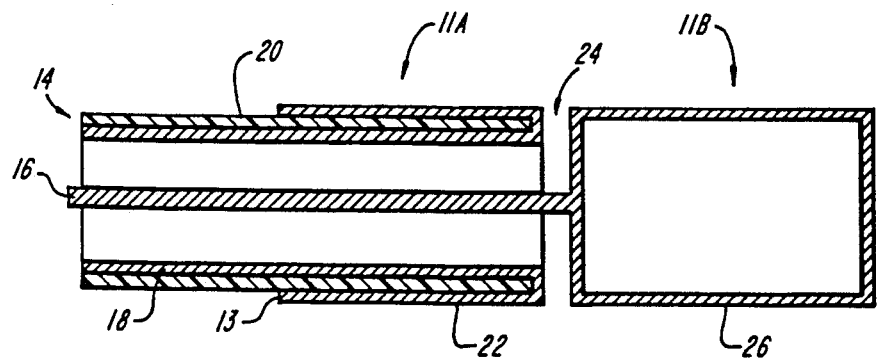
FIG. 3 is an enlarged view of a portion of the microwave instrument shown in FIG. 2.

FIG. 3 shows that the transmission line 14 is of the coaxial type with an inner conductor 16 and on outer conductor 18. The antenna 11 of the illustrated instrument 10 is a form of dipole, with two radiating elements 11A and 11B. The illustrated antenna elements 11A and 11B are aligned with one another and with the elongation of the catheter 12, thus forming a compact structure that is easy to deploy in a body cavity or passage.

The antenna radiating elements 11A and 11B also are aligned with the coaxial transmission line 14. In particular, the element 11A employs a tubular, e.g. cylindrical, conductor 22 coaxially seated outwardly over the transmission line outer conductor 18. The illustrated conductors 16, 18 and 22, thus, have a substantially triaxial geometry. The end of the conductor 22 distal from the source 13 (FIG. 1) is connected to the outer conductor 18 on one side of an antenna gap 24. A tubular sleeve or sheath 20 of insulating material having a selected dieletric constant fills the radial gap between the transmission line conductor 18 and the antenna conductor 22. The end of the conductor 22 proximal to the source 13, i.e., distal from the gap 24, has no connection to the transmission line and hence is terminated with a microwave open circuit.

This construction of the antenna element 11A forms a microwave choke that presents a selected impedance characteristic to the feed transmission line at the antenna gap 24. As known in the art, the value of this impedance characteristic is a function of the outer diameter of the conductor 18, the inner diameter of the conductor 22, the dielectric constant of the insulating sheath, the length of the conductor 22, and the frequency of operation.

With further reference to FIG. 3, the other antenna element 11B is a rod-like cylindrical conductive stub 26 that forms the other side of the antenna gap 24. The feed line inner conductor 16 extends across the gap 24, beyond the outer conductor 18, and connects to the stub 26. The outer diameter of the stub, which typically is a hollow cylindrical conductor closed at both ends with conductive disk members, preferably is the same as the outer dimension of the choke conductor 22. An outer protective sheath 27 (FIG. 2) of pliable insulating material, e.g. plastic, encloses the antenna conductors 22 and 26.

The width of the antenna gap 24 is a small fraction of the wavelength of the source current. The gap is large enough to ensure that there is no accidental contact between antenna elements 11A and 11B. Typically, the gap 24 is between approximately one and two millimeters.

Figure 4:
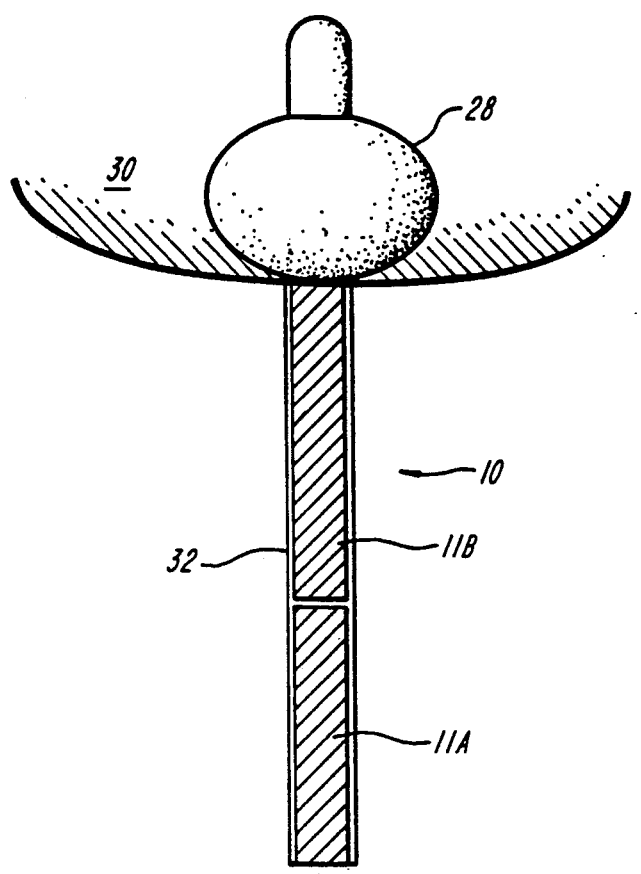
FIG. 4 is a schematic view of the microwave instrument shown in FIG. 1 positioned in a patient's urethra proximal to the patient's bladder.

A typical instrument 10 for introduction into a human by way of the urethra is constructed around a standard twelve-Fr Foley urethral drainage catheter 12 such as is manufacture by C. R. Bard of Covington, Ga. The Foley catheter has a balloon 28 which, as shown in FIG. 4, can be inflated within the bladder 30 of a patient to anchor the instrument 10 and ensure that the radiating elements 11A and 11B are located within the prostatic urethra 32.

As shown, the preferred antenna elements 11A and 11B are equal in length to form a symmetrical dipole, and are located so as to radiate from the proximal margin of the balloon over a length of four to six cm. For maximum flexibility, the conductors 22 and 26 of the elements can be formed from a fine wire braid. A suitable wire product is manufactured by New England Electric Wire of Lisbon N.H. A suitable coaxial transmission line 14 has been found to be RG-178 coaxial cable with the outer jacket removed. When this cable is used, the antenna elements 11A and 11B are configured to present an impedance to the transmission line 14 of approximately fifty ohms. Other transmission lines known to those skilled in the art can be used. When other transmission lines are used, antenna elements 11A and 11B must be configured to present an impedance that approximates the proper match for the selected transmission line. While coaxial cable is described and deemed preferable, persons skilled in the art may elect to employ other high frequency feed-lines.

Figure 5:
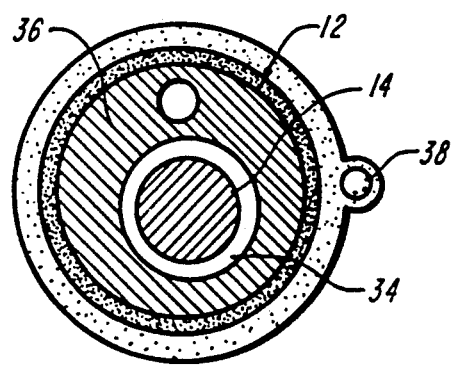
FIG. 5 is a section view taken along line 4—4 of FIG. 2.

As shown in FIG. 5, the transmission line 14 passes through the drain channel 34 in the Foley catheter 12. Connections to the antenna sections 11A and 11B are made through an exit hole made at the junction region, that is at the antenna gap 24, through the catheter wall 36. As stated, the antenna section 11B is electrically connected to the inner conductor 16 of the feed-line 14 and the antenna section 11A is electrically connected to the feed-line outer conductor 18.

The entire instrument 10 is preferably insulated up to the proximal end of the balloon 28 with, for example, a sheath 27 of polyolefin heat-shrink tubing such as that referred to as VFP-876 and manufactured by the 3M Corporation of Austin, Tex. The end of the heat shrink layer at the distal end of the antenna section 11B and the urinary drain opening 34 of the Foley catheter 12, can be sealed with silicone sealant. This ensures that the antenna elements and the feed-line are fully insulated.

FIGS. 2 and 5 show that, for monitoring purposes, the instrument 10 has an optional thermometry catheter 38 attached along the outside of the sheath 27. Attachment can be effected, for example, utilizing a silicone sealant. It is conventional that the catheter 38 includes a thermometer; a nineteen gauge thermometry catheter is deemed preferable.

An instrument having the antenna structure described above and shown in the attached drawing has the advantage over conventional interstitial dipole antennas in that the radiating element in 11A is a high-frequency choke. A theoretically ideal choke provides an infinite impedance, and hence there is no small current between the radiating element 11A and the feed-line. Such an ideal antenna operates, therefore, independently of insertion depth. In practical application, however, the choke section 11A presents a finite impedance and there is a small current between the antenna section 11A and the feed-line.

Factors affecting choke performance include the choke length, dielectric constant, source frequency, and the ratio of antenna element diameter to transmission line diameter. Design of the instrument 10, therefore, compromises clinical requirements with these features. While the ideal choke may be impractical due to overall dimension or difficulty in manipulation, the construction which this invention provides attains a clinically acceptable instrument having an effective choke.

Theoretically, for a choke length of approximately 3.2 cm., which is clinically acceptable and provides an essentially optimum radiation in tissue, and a dielectric constant of 1.7, the instrument is to be powered with alternating current at approximately 1800 MHz. This frequency has a quarter wavelength equal to the above specified choke length and hence attains a minimal level of current between the antenna element 11A and the transmission feed-line. It is necessary, however, to consider other factors. One is that the Federal Communications Commission (FCC) provides that only certain frequency bands are available for unshielded operation for Industrial, Scientific, and Medical applications (ISM). Consequently, microwave equipment designed for these applications typically operates at 433 MHz, 915 MHz, or 2450 MHz. One is required, therefore, when designing the choke element 11A to select a section length that resonates well at one of these frequencies, considering the dielectric constant of the composite tissue/catheter media.

When powered at 915 MHz, the ideal choke length, considering a dielectric constant of 1.7, is approximately 6.4 cm. This length is not, however, acceptable for clinical purposes. While a 3.2 cm choke resonates well at 915 MHz if the dielectric constant of the tissue/catheter media is 6.49, to achieve such a high dielectric constant requires a choke dielectric material such as ceramic, which is extremely brittle. This would make the manipulation and proper positioning of the instrument 10 difficult.

In view of these factors, a preferred embodiment of the instrument 10 has a section 11A length of approximately 3.2 cm. and a dielectric constant as close to 6.49 as is practical. Increasing the dielectric constant toward this ideal value moves the resonance peak of the choke to lower frequencies and thereby improves the performance of the antenna 11 at the FCC approved 915 MHz.

As stated, ideally the length of section 11A is a quarter wavelength of the operating frequency or of a frequency within the operating range. The length, then, is related to a quarter wavelength of the operating frequency In light of known dielectric materials and clinical factors, however, in practice the length of section 11A is typically less than a quarter wavelength and greater than an eighth wavelength of the source current.

Having described the invention, what is claimed as new and secured by Letters Patent in:

1. Radiant heating apparatus for deployment within an animal body to radiate heat-producing electromagnetic energy into the body, said apparatus having an antenna mounted on a catheter element and connected to an electrical transmission line having first and second conductors for feeding electrical current form a source to the antenna, said apparatus having the improvement in which
   A. the antenna comprises a first radiating element carried on said catheter element and extending from an antenna food junction in a first direction along a first elongation axis, (i) said first radiating element being an electrical choke at a frequency within said antenna operating range and being connected to said first transmission line conductor at said feed junction and presenting a first selected impedance to said feed junction, (ii) said first radiating element forming said electrical choke with a conductive element connected to said transmission line conductor and with a dielectric having a dielectric constant substantially less than that of said animal body, (iii) said first radiating element having a first length along said first direction that is substantially a quarter wavelength within said animal body at said operating frequency and said choke having a length which in said lesser dielectric constant is substantially less than a quarter wavelength at said same operating frequency, B. a second radiating element carried on said catheter element and extending form said feed junction in a second direction opposite to said first direction along said first axis, (i) said second radiating element being connected to said second transmission line conductor and presenting a second selected impedance to said feed junction, C. said first and second radiating elements radiating electromagnetic energy outwardly form said feed junction upon being excited from said transmission line with alternating electrical current within a selected frequency range, and D. said first and second radiating elements being axially disposed along said first axis for presenting said first and second impedances to said transmission feed line for providing said radiation substantially independently of the length of said catheter element inserted within the animal body beyond the full insertion of said first or second radiating elements within the animal body.

2. Radiant heating apparatus according to claim 1 having the further improvement wherein said first and second impedances are substantially equal.

3. Radiant heating apparatus according to claim 1, having the further improvement wherein the lengths of said first and second radiating elements along said first axis are substantially equal.

4. Radiant heating apparatus according to claim 1 further comprising a first radiating element being a tubular conductor coaxially seated outwardly over said outer conductor of said transmission feed line and having (i) a first end proximal to said feed junction and connected to said outer conductor at said first end thereof, (ii) a second end distal from said feed junction and extending opposite to said first end along said outer conductor wherein said tubular conductor forms part of said electrical choke, and (iii) said second end of said first radiating element presents to said feed junction a high impedance.

5. Radiant heating apparatus for deployment within an animal body to radiate heat-producing electromagnetic energy into the body, said apparatus having an antenna mounted on a catheter element and connected to an electrical transmission line having inner and outer coaxial conductors for feeding electrical current from a source to the antenna, said apparatus having the improvement in which A. the antenna comprises a first radiating element carried on said catheter element and extending form an antenna feed junction in a first direction along a first elongation axis, (i) said first radiating element being an electrical choke at a frequency within said antenna operating range and being a tubular conductor coaxially seated outwardly over said outer conductor to form, in cooperation with said inner conductor, a substantially triaxial geometry, said first radiating element being connected to said outer conductor at said feed junction and presenting a first selected impedance to said feed junction, (ii) said first radiating element forming said electrical choke with a conductive element connected to said first transmission line conductor and with a dielectric element having a dielectric constant substantially less than that of said animal body, (iii) said first radiating element having a first length along said first direction that is substantially a quarter wavelength within said animal body at said operating frequency and said choke having a length which is said lesser dielectric constant is substantially less than a quarter wavelength at said same operating frequency, B. a second radiating element carried on said catheter element and extending from said feed junction in a second direction opposite to said first direction along said first axis, said second radiating element being connected to said inner conductor and presenting a second selected impedance to said feed junction, C. said first and second radiating elements radiating electromagnetic energy outwardly from said feed junction upon being excited from said transmission line with alternating electrical current within a selected frequency range, and D. said first and second radiating elements being axially disposed along a first elongation axis for presenting said first and second impedances to said transmission feed lien for providing said radiation substantially independently of the length of said catheter element inserted within the animal body beyond the full insertion of said first or second radiating elements within the animal body.

6. Radiant heating apparatus according to claim 5 having the further improvement wherein said first and second impedances are substantially equal.

7. Radiant heating apparatus according to claim 5, having the further improvement wherein the lengths of said first and second radiating elements along said first axis are substantially equal.

8. Radiant heating apparatus according to claim 5 further comprising a first radiating element being a tubular conductor coaxially seated outwardly over said outer conductor of said transmission feed lien and having (i) a first end proximal to said feed junction and connected to said outer conductor at said first end thereof, (ii) a second end distal from said feed junction and extending opposite to said first end along said outer conductor wherein said tubular conductor forms part of said electrical choke, and (iii) said second end of said first radiating element presents to said feed junction a high impedance.

* * * * *